United States Patent
Hawman

(10) Patent No.: US 7,521,681 B2
(45) Date of Patent: Apr. 21, 2009

(54) NON-ROTATING TRANSAXIAL RADIONUCLIDE IMAGING

(75) Inventor: Eric Grant Hawman, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 164 days.

(21) Appl. No.: 11/771,159

(22) Filed: Jun. 29, 2007

(65) Prior Publication Data

US 2009/0001273 A1    Jan. 1, 2009

(51) Int. Cl.
*G01T 1/166* (2006.01)
(52) U.S. Cl. .................................. 250/363.04
(58) Field of Classification Search . 250/363.01–363.1; 378/147
See application file for complete search history.

(56) References Cited

U.S. PATENT DOCUMENTS 4,419,585 A * 12/1983 Strauss et al. ............ 250/505.1

OTHER PUBLICATIONS

Novak et al. "Experimental measurement of axial and transaxial resolutions of a slit-slat collimator and comparision to theoretical expectations," 2006, IEEE Nuclear Sceince Symposium Conference Record, vol. 3, pp. 1832-1836.*

* cited by examiner

*Primary Examiner*—David P Porta
*Assistant Examiner*—Kiho Kim
(74) *Attorney, Agent, or Firm*—Peter L. Kendall

(57) ABSTRACT

Transaxial radionuclide imaging is implemented without relative rotation between detectors and a patient by employing a collimator comprising segments sharing a common central axis, each segment having a plurality of apertures extending therethrough, wherein the segments are angularly displaced from one another about the common central axis. Embodiments include SPECT systems comprising a polygonal detector having a collimator on at least two sides thereof. Embodiments further include collimators comprising six segments, each offset by an angle of 7 to 9°.

19 Claims, 7 Drawing Sheets

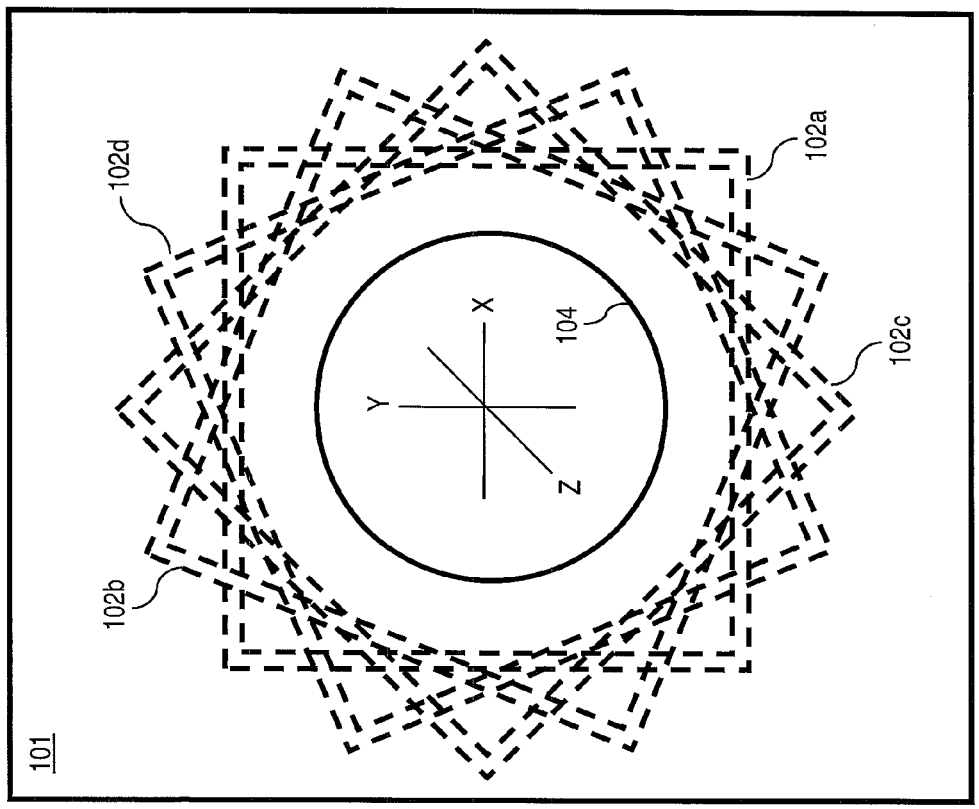
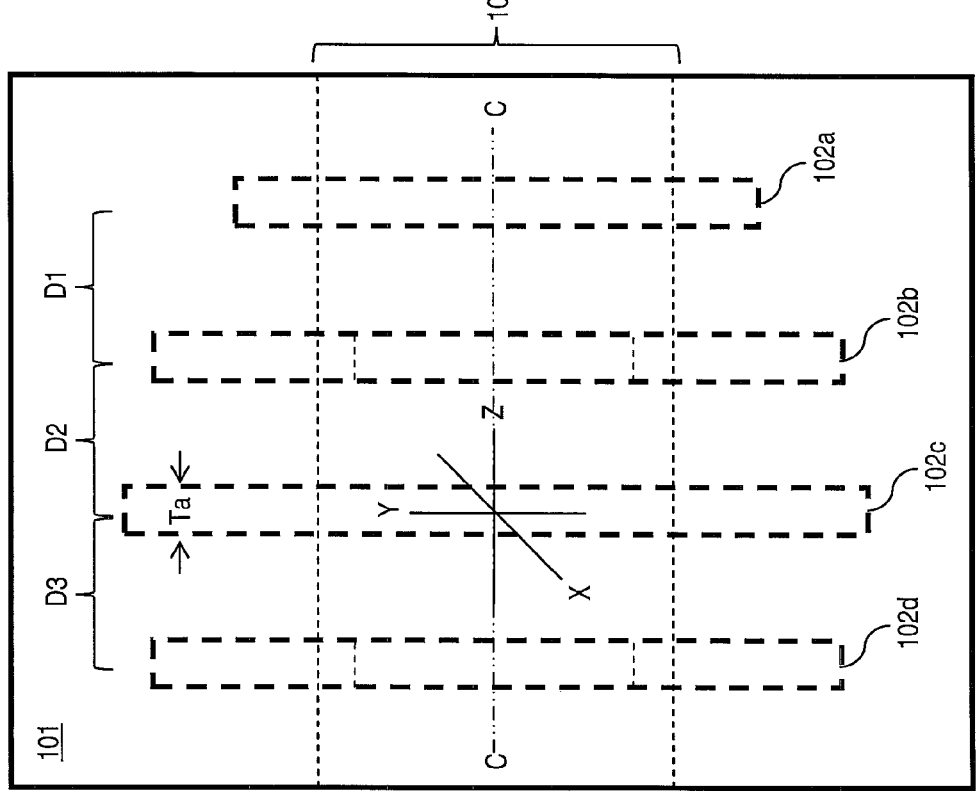

NON-ROTATING TRANSAXIAL RADIONUCLIDE IMAGING

FIELD OF THE INVENTION

The present invention relates to radionuclide imaging. The present invention is particularly applicable to mechanisms for directionally filtering incident gamma quanta upon detectors (or cameras) within diagnostic imaging apparatuses, such as those used in single photon emission computed tomography (SPECT) systems.

BACKGROUND OF THE INVENTION

Medical radionuclide imaging, commonly referred to as nuclear medicine, is a significant diagnostic tool that involves the use of ionizing radiation to obtain accurate, three-dimensional (3D) maps of an in vivo patient. Typically, one or more biologically appropriate radiopharmaceuticals are administered to a patient, as by ingestion, inhalation, or injection. Tracer amounts of these radioactive substances emanate gamma quanta while localizing at specific organs, bones, or tissues of interest (hereinafter collectively referred to as the "study area") within the patient's body. One or more radiation detectors are then used to record the internal spatial distribution of the radiopharmaceutical as it propagates from the study area.

As the information is aggregated, it may be processed to create "static" 3D images of the study area. Temporal changes in the distribution's flux may be recorded to generate "dynamic" 3D images. When appropriately interpreted, these "maps" of the patient provide trained physicians insight into the patient's ultimate clinical diagnosis and/or treatment. Known applications of nuclear medicine include: analysis of kidney function, imaging blood-flow and heart function, scanning lungs for respiratory performance, identification of gallbladder blockage, bone evaluation, determining the presence and/or spread of cancer, identification of bowel bleeding, evaluating brain activity, locating the presence of infection, and measuring thyroid function and activity.

In order to screen out undesired, "background" radiation, conventional radionuclide imagers typically provide some means to restrict the ionizing paths of detected gamma quanta to those modes of propagation lying within a predefined range of acceptance angles. Such means typically comprise a set of barriers located in the direction of the ionizing source to substantially exclude gamma quanta not emanating along the direct paths from the study area to the radiation detector. Collimators, including an array of apertures, are customarily employed for this purpose.

Collimators are typically positioned so that undesired radiation is substantially absorbed before it can be detected. The direction (or incident angle) of unabsorbed gamma quanta is controlled by way of collimating aperture arrays that filter a radiation field before gamma quanta is detected. Collimators are typically manufactured from relatively dense (or high atomic number) materials so that undesired radiation is adequately stopped (or absorbed) before reaching the imaging detector. A variety of collimators exist, such as parallel-hole, converging (or diverging) hole, slant-hole, fan-beam, and pin-hole, as well as arrays thereof. These collimators come in a variety of materials, aperture diameters, aperture shapes, and thicknesses of aperture partitions, i.e., septa thicknesses.

One such radionuclide imaging technology that incorporates collimators is the gamma camera utilized in single photon emission computed tomography (SPECT) scanning. In SPECT scanning, a subject (or patient) is infused with a radioactive substance that emits gamma rays. Conventionally, a gamma camera includes a transducer to receive the gamma rays and record an image therefrom. In order for the image to be a true representation of the subject, a collimator having collimating apertures is positioned between the transducer and the subject to screen out all of the gamma rays expect those directed along a straight line through the collimating apertures between a particular part of the subject and a corresponding particular part of the transducer. Traditionally, the collimator is made of radiation opaque material, such as tungsten, tantalum, or lead, and collimating apertures have been formed therein.

For SPECT imaging to be realized, system designs generally require the gamma cameras to be supported on gantries that rotate the detectors through a specific angular range about the patient, usually covering one hundred eighty to three hundred sixty degrees of rotation. A drawback associated with this requirement, however, is that such gantries are relatively expensive subsystems of the diagnostic tool, because they must be capable of providing rapid rotation of large, heavy camera heads through very precise orbits about the patient.

Therefore, there exists a need for simplified medical radionuclide imaging apparatuses that can be economically and efficiently manufactured. There exists a particular need for such apparatuses that provide high image quality without camera head rotation.

DISCLOSURE OF THE INVENTION

An advantage of the present invention is a collimator for use in medical imaging, particularly SPECT imaging, wherein the collimator is structured so that it is not necessary to rotate the radiation detectors relative to the patient.

Another advantage of the present invention is a nuclear medical imaging device that can be manufactured efficiently and at a significantly reduced cost.

A further advantage of the present invention is a radionuclide imaging method comprising linearly displacing a patient along a longitudinal axis without relative rotation between the radiation detectors and patient.

Additional advantages and other features of the present invention will be set forth in the description which follows and in part will be apparent to those having ordinary skill in the art upon examination of the following or may be learned from the practice of the present invention. The advantages of the present invention may be realized and obtained as particularly pointed out in the appended claims.

According to the present invention, the foregoing and other advantages are achieved in part by a collimator comprising a plurality of adjacently stacked collimating segments sharing a common central axis, wherein, adjacent collimating segments are annularly displaced from one another about the common central axis.

Another advantage of the present invention is a radionuclide imaging method comprising: positioning a patient having a radiating mass within a single photon emission computed tomography (SPECT) system and moving the patient along a longitudinal axis, the SPECT system comprising: a polygonal-shaped radiation detector; and a collimator on at least two sides of the polygonal-shaped detector, wherein the collimator comprises a plurality of adjacently stacked collimating segments sharing a common central axis, each segment having a plurality of apertures extending therethrough, wherein the adjacent collimating segments are angularly displaced from one another about the common central axis; wherein each aperture forms a passageway for radiation rays emanating from the radiating mass in a direction substantially aligned with a longitudinal axis of the respected passageway so that aligned radiation rays strike the detector; and motive means for effective longitudinal relative motion between the detector and the patient for taking multi-angular SPECT radiation sampling of the radiating mass in the patient utilizing the passageways, without relative rotation between the patient and detector.

A further advantage of the present invention is a nuclear medical imaging apparatus comprising: a gantry defining a central axis; a plurality of detection rings disposed about the axis and supported by the gantry; and a plurality of radiation detectors disposed among the plurality of detection rings and configured to detect ionizing radiation, wherein the adjacent rings are longitudinally and angularly displaced from one another along the axis.

A further advantage of the present invention is a radionuclide imaging method comprising: administering a radiopharmaceutical to a subject; linearly displacing the subject through a series of concentric detection bands, the bands including one or more stationary gamma cameras configured to detect gamma rays emanating from the subject; collimating gamma rays emanating from the subject through a series of stacked collimating segments angularly displaced from one another about a common axis of rotation and positioned between the subject and the one or more gamma cameras; and recording gamma ray occurrences detected at the one or more gamma cameras, wherein there is no relative rotation between the subject and the concentric detection bands.

Additional advantages of the present invention will become readily apparent to those skilled in the art from the following detailed description, wherein embodiments of the present invention are described, simply by way of illustration of the best mode contemplated for carrying out the present invention. As will be realized, the present invention is capable of other and different embodiments and its several details are capable of modifications in various obvious respects, all without departing from the present invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 2a, 2b, and 2c are a side and two front views schematically illustrating a plurality of longitudinally displaced polygon detection rings of the imaging system, in accordance with an embodiment of the present invention;

DESCRIPTION OF THE INVENTION

Figure 1:
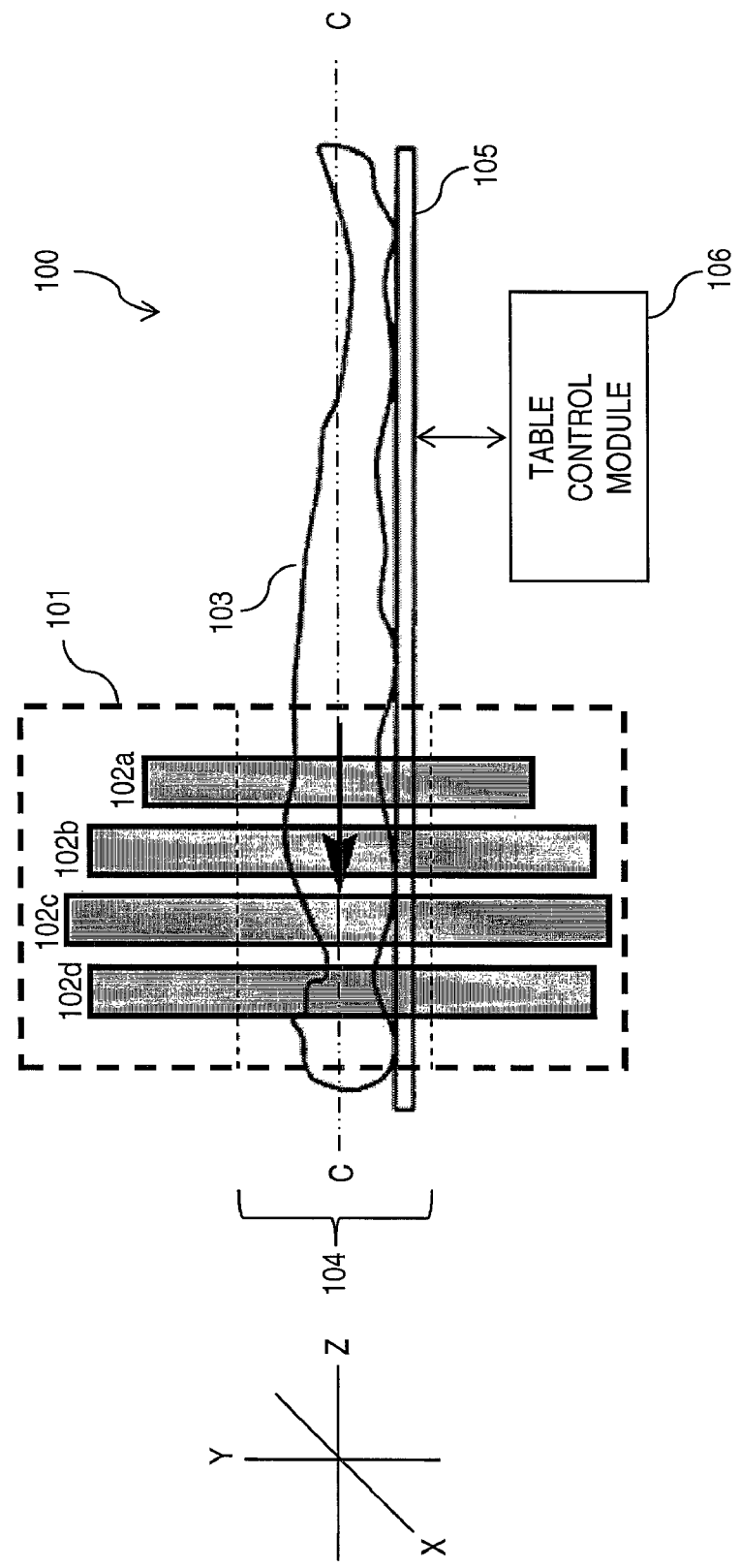
FIG. 1 schematically illustrates a non-orbiting transaxial radionuclide imaging system, in accordance with an embodiment of the present invention.

The present invention addresses the need for nuclear medical imaging devices that can be manufactured efficiently and at reduced cost. Embodiments of the present invention achieve that objective by providing collimators that can be used in various types of nuclear medical imaging devices, such as those employed in SPECT scanning, without the necessity of causing relative rotation between the detectors and patient. In this way, the use of expensive gantry systems to support and rotate heavy detectors, such as gamma cameras, around the patient is avoided. Thus, in accordance with embodiments of the present invention, effective and accurate imaging is performed simply by causing linear movement of the patient along a longitudinal axis, without causing relative rotation between the detectors and patient.

In accordance with embodiments of the present invention, a collimator is provided comprising a plurality of stacked parallel collimating segments, each containing a plurality of apertures extending therethrough, the adjacent collimating segments being angularly displaced from one another about a central common axis. Embodiments of the present invention include collimators having any number of collimating segments, including 3 through 10, such as 5 through 9, e.g., 6 to 8. In an embodiment of the present invention, a collimator is provided with 7 segments capable of scanning 45°, each segment being offset by 6.4°.

Imaging systems in accordance with embodiments of the present invention typically comprise detection rings having a polygonal shape, such as rectangular, or octagonal, with a collimator having the plurality of offset segments on at least two sides thereof. In accordance with embodiments of the present invention, the detection rings need not completely encompass or surround a patient during imaging. For example, a rectangular or square shaped detector can be provided with only two sides, thereby avoiding unnecessary confinement of the patient during imaging. When using octagonal shaped rings, 2 through 5 of the sides of an octagonal ring may be employed as well, thereby avoiding unnecessary confinement of the patient.

In accordance with embodiments of the present invention, the apertures formed within a collimating segment have a collimation angle of between 0° and +10°, such as between +4° and +6°. Accordingly, as a patient is moved along a longitudinal axis of a device through a series of detectors comprising collimators, a complete scan (set of views for tomographic reconstruction) of the patient can be obtained. It should be noted that dependent upon the target area, e.g., heart, lung, or brain, the axial coverage can be controlled between 100° and 200° to focus on the target area, e.g., 180°.

Collimators in accordance with embodiments of the present invention can be fabricated by conventional techniques employing 20 to 40 lead foils per segment as a corrugated stack. However, in embodiments of the present invention each segment is strategically rotated and the apertures therethrough strategically angled so that during imaging relative motion between the detectors and patient is not required.

FIG. 1 schematically illustrates a non-orbiting transaxial radionuclide imaging system in accordance with an embodiment of the present invention. In one particular implementation, the radionuclide imaging system comprises a non-rotating transaxial single photon emission computed tomography (SPECT) apparatus. While specific reference will be made thereto, it is to be appreciated that the present invention also finds application in other non-invasive investigation techniques and imaging systems such as nuclear tomography, coincidence imaging, emission computed tomography (ECT), single photon planar imaging, whole body nuclear scans, positron emission tomography (PET), digital x-ray computed tomography (CT), and other like diagnostic modes.

Figures 5A, 5B:
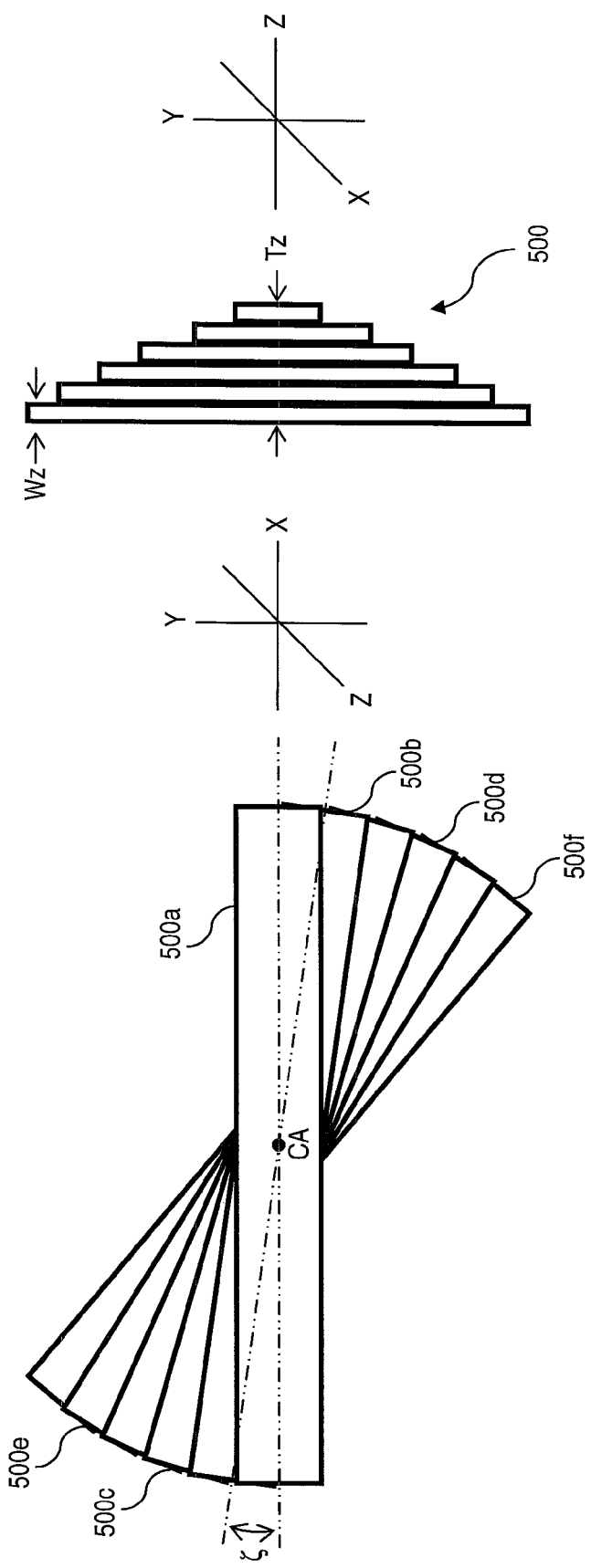
FIGS. 5a and 5b are, respectively, a side and front view schematically illustrating exemplary twister type collimator arrays, in accordance with an embodiment of the present invention.

Adverting to FIG. 1, system 100 includes a radiation detector assembly 101 (or gantry) comprising a multiplicity of radiation detectors (or gamma cameras) positioned among a plurality of axially displaced, stationary polygon detection rings 102a-102d. As such, in-plane (longitudinal) collimation is provided in the Z-Y plane by the plurality rings 102a-102d that circumferentially surround an ionizing subject or patient 103, typically enveloping one hundred eighty to three hundred sixty degrees of rotation, e.g., 180°. Further, cross-plane (axial) collimation is provided in the X-Y plane at each of the radiation detectors (not shown), or gamma cameras, by way of a plurality of "twister" type collimator arrays (FIG. 5a). Twister type collimator arrays comprise a plurality of collimating bars manufactured from photon-attenuating material bars extending over an angular range similar to that of the radiation detector rings (typically 180° to 360°) and are oriented perpendicular to the longitudinal Z-axis, thus parallel to a transaxial plane.

The stationary array of polygon detection rings 102a-102d are enclosed within and supported by gantry 101. Rings 102a-102d may be either longitudinally displaced from one another at constant or variable distances or may abut one another to form a relatively contiguous detection entity. Further, rings 102a-102d may be angularly rotated (about axis C-C) from adjacent rings at constant or variable degrees of rotation. In this manner, the multiplicity of stationary radiation detectors are disposed at predefined viewing radiuses about axis C-C and further, distributed axially among the plurality of rings 102a-102d to provide a sufficient number of angular views from which a three-dimensional (3D) radionuclide image may be reconstructed. Thus, gantry 101 does not require (but may include) traditional radiation detectors that require an orbiting path about axis C-C to acquire sufficient imaging information. The plurality of detection rings 102a-102d is described in more detail with respect to FIGS. 2a-2c. Exemplary twister type collimators are described in accordance with FIGS. 3a-5c.

With continued reference to FIG. 1, gantry 101 also includes stationary bore 104 that is optically opaque, but generally transmissive to ionizing radiation originating within its enclosed volume. Therefore, a human subject disposed within bore 104 will be prevented by the gantry's housing from observing the skeletal components of the system. During imaging, subject 103 (typically a prone human patient) is longitudinally displaced through bore 104, from ring 102a to ring 102d (or vice versa) or through any portion thereof, utilizing support table 105. In this manner, a table control module 106 may be utilized to regulate the rate at which, or stepwise displacement of, table 105 during imaging procedures.

Table control module 106 may comprise an electric motor (not shown) actuated by a servo-mechanism or processor (not shown) to displace table 105 in the longitudinal direction parallel to axis C-C. In the alternative, subject 103 may be held stationary and gantry 101 and/or the plurality of polygon detection rings 102a-102d may be longitudinally displaced over the length of subject 103. The circumferential viewing radiuses of the detectors may be larger than an inner radius of bore 104, thus allowing subjects of various sizes and shapes to traverse the entire longitudinal distance of bore 104. As in conventional medical imaging devices, bore 104 can be manufactured large enough to admit a human subject of various sizes ranging from 0 to 1 m in diameter.

Figure 2C:
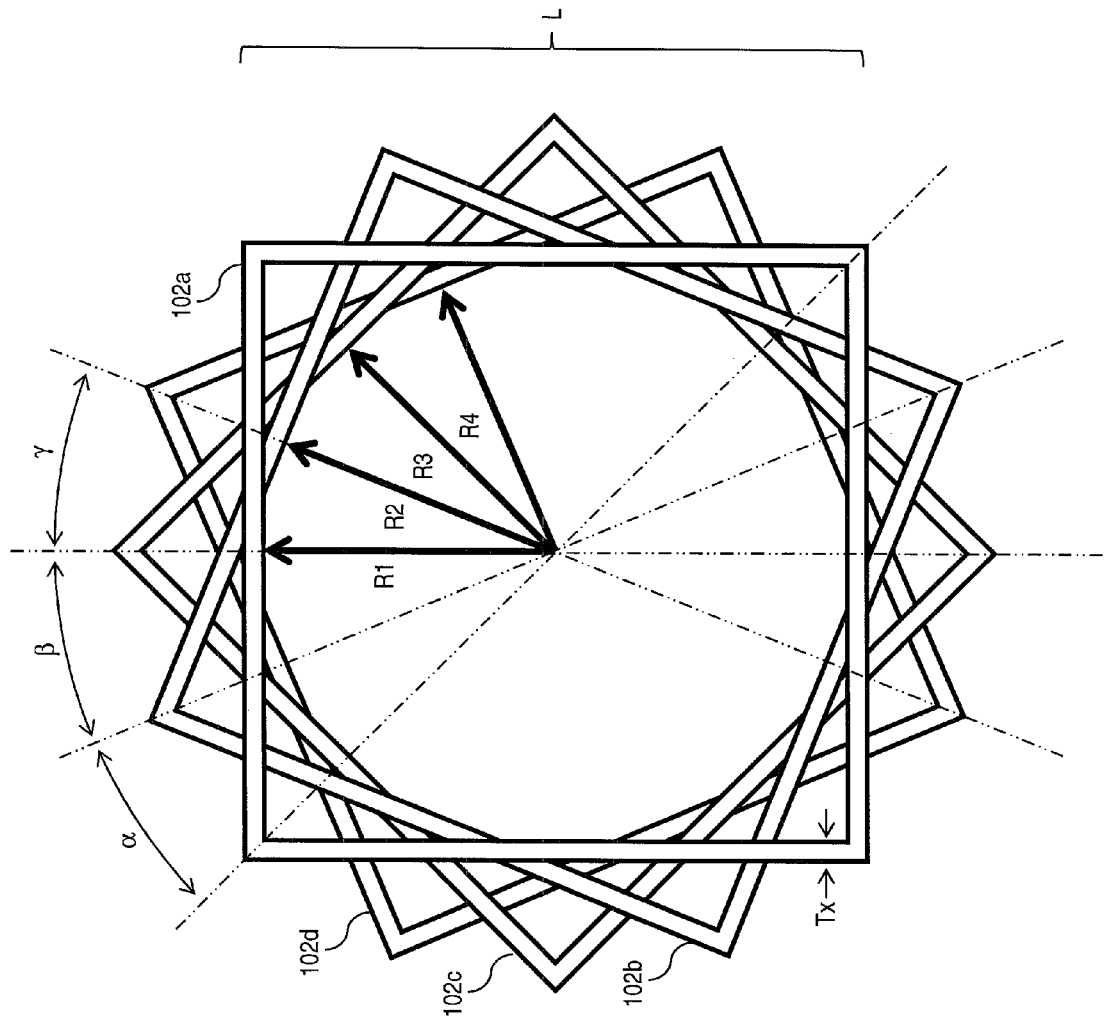
Figure 3A:
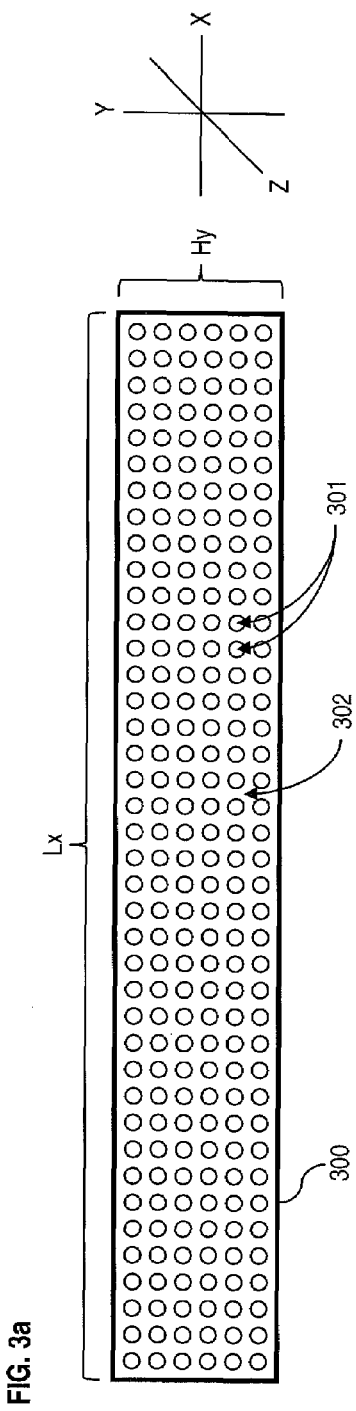
FIGS. 3a and 3b are front views schematically illustrating twister type collimator bars (or portions thereof) for incorporation within twister type collimator arrays, in accordance with various embodiments of the present invention.
Figure 3B:
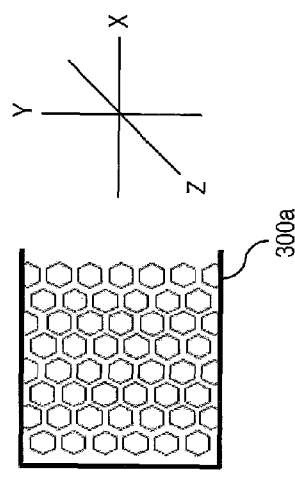

With continued reference to FIG. 1, and further reference to FIGS. 2a-c, imaging is performed after subject 103 is administered (typically by ingestion, inhalation, or injection) one or more biologically suitable radiopharmaceuticals or radioisotopes, such as $^{99m}Tc$ or $^{201}Tl$. The radiopharmaceutical is tailored to concentrate at specific organs, bones, or tissues of interest. As such, tracer amounts of these radioactive substances emanate gamma quanta relating to the internal spatial distribution of the radioisotope within subject 103. As subject 103 is longitudinally displaced through stationary bore 104, one or more radiation detectors employing one or more "twister" type collimator arrays may be used to record this internal spatial distribution as the gamma quanta propagate from subject 103.

FIGS. 2a-2c are a side and two front views schematically illustrating a plurality of axially displaced polygon detection rings of the imaging system, in accordance with an embodiment of the present invention. With respect to conventional SPECT imaging, one or more radiation detectors are typically supported on a rotating gantry that orbits the camera heads through a specific angular range about the subject, usually covering 180° to 360° of rotation. A drawback associated with this arrangement, however, is that such gantries are relatively expensive subsystems of the overall tomography system since the gantry must swiftly rotate large, heavy gamma camera heads through precise orbital paths. In an effort to remedy this deficiency, one embodiment of the present invention is directed toward obtaining various angular views of subject 103 in the longitudinal direction utilizing a stationary array of polygonal detection rings 102a-102d supporting a plurality of stationary radiation detectors at predefined axial and longitudinal distances within gantry 101. As such, only one-dimensional relative linear motion between the radiation detectors and the subject 103 need be required.

In the depicted embodiments of FIGS. 2a-2c, radionuclide imaging is performed utilizing four square radiation detector rings 102a-102d supporting a plurality of radiation detectors (not shown) coupled to a "detection face" of each ring's perimeter. Each individual ring is similarly manufactured with edge length L, edge thickness Tx, and longitudinal ring depth Ta. In an exemplary embodiment, ring dimensions may vary according to the following dimensions: L=30 to 50 cm, Tx=2 to 4 cm, and Ta=12 to 20 cm. It is to be appreciated; however, that the number of detection rings is only limited by system dimensioning and/or economic cost constraints. Moreover, it should also be apparent that each individual detection ring may be manufactured in any polygonal form (whether triangular, rectangular, pentagonal, hexagonal, etc.) with sufficient detection face surface area to support one or more radiation detectors of the present invention. In turn, it is not necessary for the detection rings to wholly encompass the circumferential distance about axis C-C, i.e., any portion of a detection ring may be utilized so long as that portion can support one or more radiation detectors and can also be supported at a predefined angular view within gantry 101. Moreover, individual detection ring shaping or dimensioning may vary from one ring to another. Therefore, any number of polygonal detection rings may be incorporated into system 100 and may optionally be varied in form, size, or shape from one ring to another.

Additionally, rings 102a-102d are longitudinally displaced from one another along the Z-axis at predefined distances D1, D2, and D3, wherein D1=D2=D3≈0 to 15 cm. The rings 102a-102d are also angularly rotated about axis C-C (the Z-axis) from adjacent rings at annular degrees of rotation α, β, and γ, wherein α=β=γ≈1 to 10°. Further, detector rings 102a-102d may respectively support four to nine collimator bars (not shown), in certain embodiments, at fixed viewing radii R1, R2, R3, and R4, wherein R1=R2=R3=R4≈16 to 50 cm. It is to be appreciated, however, that both the longitudinal and annular displacement of rings 102a-102d may vary from one ring to another. In other embodiments, the detection rings may abut X-Y planar surfaces to form a relatively contiguous detection entity. Moreover, it should be apparent that the number of radiation detectors is merely limited by system dimensioning and/or economic cost constraints. As such, as the form, size, and shape of the polygonal detection rings vary, so too will the fixed viewing radii of the plurality of radiation detectors and collimators utilized. Accordingly, as the number of collimation bars supported on differing detection faces of the polygon rings increases, the overall number of detection rings may decrease without compromising angular sampling.

To achieve a predefined number of angular samples (or integral plane projection views) at the fixed viewing radii of detection rings $102a$-$102d$ utilizing system 100, the plurality of radiation detectors are collimated through the employment of "twister type" collimators. A twister type collimator is meant to convey a collimator whose direction of view changes in a regular (or stepwise) manner as a function of the axial dimension (depth or z-coordinate) of the collimator. This may be achieved through the use of a set of polygonal collimator bars whose collimating apertures are perpendicular to the sides of the polygonal detection rings $102a$-$102d$.

A set of collimating bars may be attained by stacking a plurality of collimating polygonal shaped rings, angularly displaced from one another much like detection rings $102a$-$102b$, such that two or more angularly displaced collimating rings may be circumscribed within each of the plurality of detection rings $102a$-$102d$. Thus, each side of a polygonal collimating ring comprises a narrow collimating bar of approximate dimensions: L=30 to 50 cm, Tx=2 to 4 cm, and Tz=2 to 4 cm. In exemplary embodiments of the present invention, collimating arrays may comprise four to nine stacked collimating rings angularly displaced from one another. Thus, the plurality of polygonal collimating rings may comprise bars defining an axial depth whose direction of view varies with respect to such dimensioning characteristics.

FIGS. 3$a$ and 3$b$ are front views schematically illustrating twister type collimator bars (or portions thereof) for incorporation within twister type collimator arrays, in accordance with various embodiments of the present invention. A collimator bar 300 may be manufactured from a relatively dense (or high atomic number) material, such as lead, tantalum, tungsten, or other like gamma quanta absorbing material, so that undesired radiation can be adequately stopped (or obstructed) before reaching a radiation detector. Any known collimator manufacturing technique may be utilized to fabricate collimator bar embodiments of the present invention including, but not limited to: die casting, permanent mold casting, powdered metal techniques, extruding, lead filled epoxy techniques, drilling, corrugated foil lamination, chemical and photo etching, laser cutting, sputter depositing, electrical discharge machining, stereolithography, as well as other similar fabrication methods.

As depicted within FIG. 3$a$, collimator bar 300 has dimensions equivalent to length Lx, height Hy, and width Wz (extending into the page), and comprises a plurality of apertures 301 of predefined diameter, shape, and distribution, which extend through bar 300. Such aperture distributions form passageways for ionizing gamma quanta and may be arrayed in repeating or staggered rows and columns or in other like distributing manners. Adjacent apertures 301 are separated by septa 302 of sufficient width and thickness to absorb incident off-axis gamma quanta, i.e., undesired ionizing radiation. Ionizing on-axis gamma quanta (i.e., relative propagation into the page) pass through apertures 301, thereby creating collimated beams of gamma quanta at an exit face of collimator bar 300. Furthermore, since collimator bars 300 have thickness Wz, aperture passageways are channel-like, each having its own longitudinal axis that is substantially aligned with the collimated gamma quanta being permitted to pass through the various channels. In order to effectuate a desired alignment between each channel and respective gamma quanta that pass therethrough, the longitudinal axis of the channels are to be kept perpendicularly oriented with respect to the z-axis. In alternative embodiments of the present invention, these passageways may incorporate slant-angle and/or conical passageways for focusing the radiation detector assembly to specific focal points within subject 103.

As such, there is some permissible leeway in the precision of manufacturing twister type collimator bars 300 as described hereto. For use with conventional gamma cameras, the diameter of aperture 301 may vary from 0.5 to 1.5 mm. Collimator bar 300 width Wz may vary from 1 to 4 cm. Meanwhile, collimator bar length Lx may range from 30 to 50 cm and collimator bar height Hx may range from 2 to 4 cm. In alternative embodiments, aperture dimensioning and spacing may vary from aperture to aperture or arrays of apertures therein.

Figure 4A:
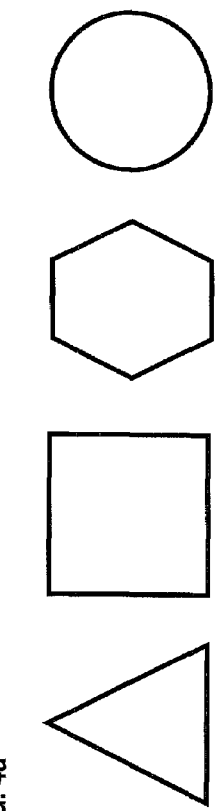
FIG. 4a schematically illustrates various aperture cross-sections utilized in (or among) alternative twister type collimator bars, in accordance with an embodiment of the present invention.
Figure 4B:
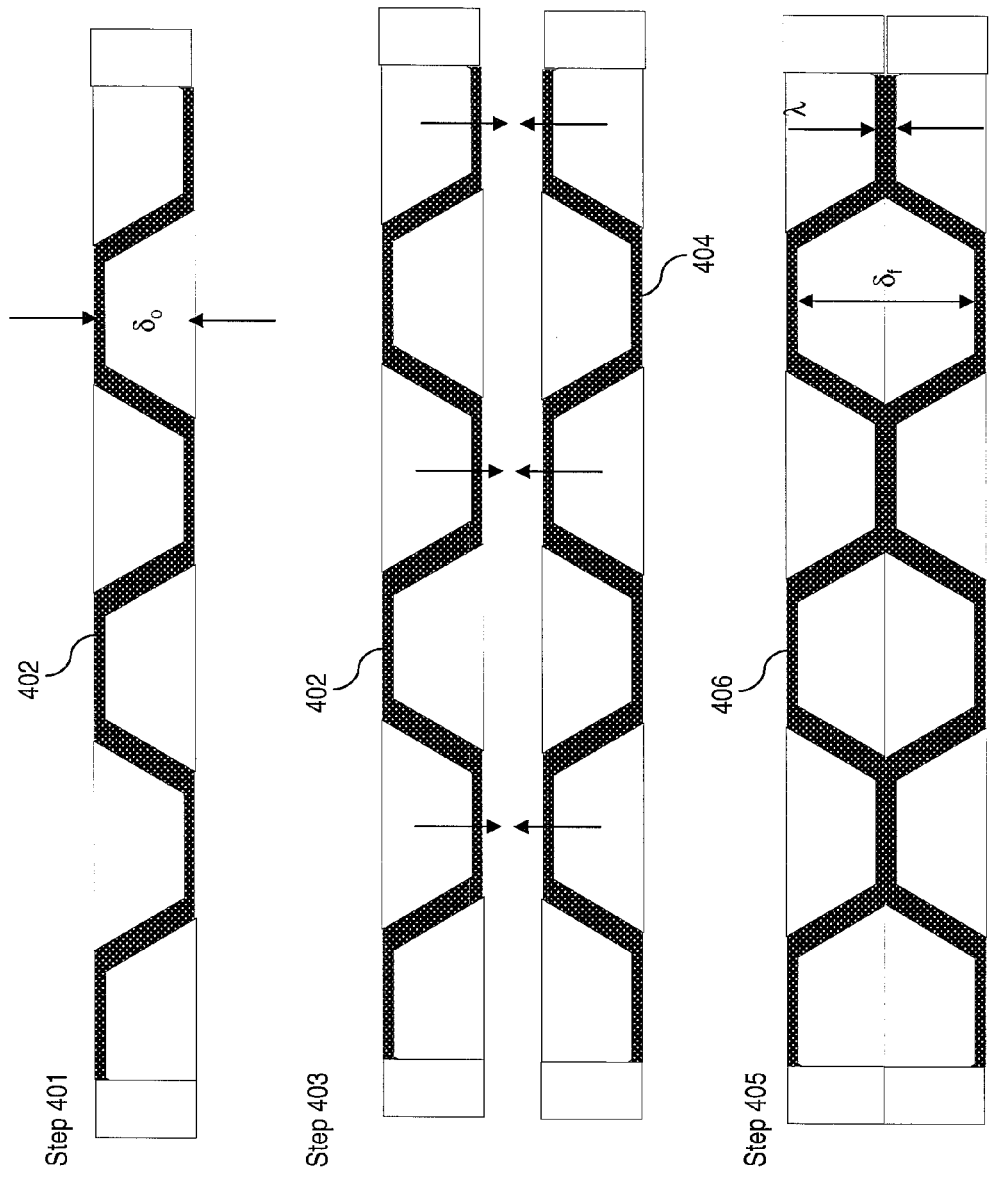
FIG. 4b schematically illustrates an exemplary method of forming hexagonal apertures within a collimating bar, in accordance with an embodiment of the present invention.

Included within FIG. 4$a$ are various alternative schematic illustrations of aperture cross-sections that may be utilized in conjunction with twister type collimator bars, in accordance with various embodiments of the present invention. The purpose of FIG. 4 is to convey the fact that possible aperture cross-sections are only limited to those capable of being manufactured using those methods previously described. As such, almost any conceivable cross-section may be incorporated into twister type collimator bars.

FIG. 3$b$ illustrates a portion of an alternative collimator bar 300$a$ incorporating hexagonal aperture cross-sections distributed in staggered rows and columns, in accordance with an embodiment of the present invention. Referring back to FIG. 3$a$ and with continued reference to FIG. 3$b$, such an exemplary collimator bar 300$a$ may be manufactured from die pressed and adhesive laminated lead foils of dimensions Lx=30 to 50 cm, Hy=0.6 mm (for and single form foil strip), Wz=1 to 4 cm, with final dimensions of a bar: Lx=30 to 50 cm, Hy=2 to 4 cm, Wz=1 to 4 cm, and hexagonal aperture cross-sectioning of diameter=1 mm. As such, collimator bar 300$a$ will comprise approximately 40 individual foils defining approximately 300 collimating apertures.

FIG. 4$b$ schematically illustrates an exemplary method of forming hexagonal apertures within a collimating bar, in accordance with an embodiment of the present invention. At step 401, lead foil 402 is formed with half-hexagonal corrugations using one of the aforementioned manufacturing procedures, such as die pressing. In this manner, formed corrugations will be displaced by $\delta_o$ from the original foil form, wherein in an exemplary embodiment $\delta_o$ is approximately 0.6 mm (but may be sized and varied according to design consideration and application). Similarly, additional corrugated lead foils will be manufactured such as lead foil 404. As such, lead foils of type similar to lead foil 402 may be considered "male" lead foils and lead foils of similar type to lead foil 404 may be considered "female" lead foils.

At step 403, lead foils 402 and 404 may be stacked upon one another to form one or more hexagonal aperture arrays. As depicted, individual apertures are still "open" only as a method of illustrating the stacking procedure. At step 405, a stacked pair of lead foils, i.e., male lead foil 402 is stacked upon female lead foil 404, may be coupled together using any of the aforementioned methods, such as lamination or gluing, resulting in collimating stack 406.

In the illustrated embodiment, collimating stack 406 comprises hexagonal apertures in a uniform array across the length of collimating stack 406. It is to be appreciated; however, that differing or alternating arrays of hexagonal apertures may be incorporated into collimating stack 406. After the coupling procedure, collimating stack 406 comprises hexagonal apertures of diameter $\delta_f$ and septa thickness $\lambda$, wherein in an exemplary embodiment $\delta_f$ is approximately 1 mm and $\lambda$ is approximately 0.2 mm. Finally, multiple collimating stacks will be stacked upon one another and coupled to form a collimating bar, such as that illustrated in FIG. 3b. While hexagonal apertures were formed, it is to be appreciated that other polygonal cross-sections may be incorporated such as those depicted in FIG. 4a. Further, aperture arrays may vary across the length width, and depth of the resulting collimating bar.

Moreover, it is to be appreciated that the number, diameter, shape, and distribution of apertures 301 may be predetermined to form a parallel beam of gamma quanta having a uniform or substantially uniform cross-sectional sensitivity (response profile) during imaging. Moreover, collimator bar 300 may be configured to produce collimated beams of gamma quanta exhibiting one or more non-uniform sensitivity distributions.

FIGS. 5a and 5b are, respectively, a side and front view schematically illustrating exemplary twister type collimator arrays, in accordance with various embodiments of the present invention. To realize a desired angular sampling for system 100, six collimator bars 500a-500f are exemplarily stacked in a twisting array as depicted within FIG. 5a. Adjacent collimator bars may be coupled to one another through known coupling or adhesion techniques, such as lamination, to share a common annular axis of rotation CA extending out of the page and located at a horizontal and vertical midpoint of each collimator bar 500a-500f. Accordingly, adjacent collimator bars may be angularly rotated about axis CA at annular degrees of rotation $\zeta$, wherein $\zeta$ may vary from 1 to 10°. In the depicted embodiment, collimator bars are angularly rotated at $\zeta \approx 8°$. It should be appreciated; however, that the annular degrees of rotation $\zeta$ may be held constant or vary from one collimator bar to another. Further, the common annular axis of rotation CA may be orientated at any point over the X-Y facial surface of the collimator bars. In other embodiments, a lesser or greater number of collimator bars may be employed to comprise a twister type collimator array. Still further, individual collimator bars may be subdivided and stacked so as to minimize the total thickness Tz of the resulting array 500.

Figure 5C:
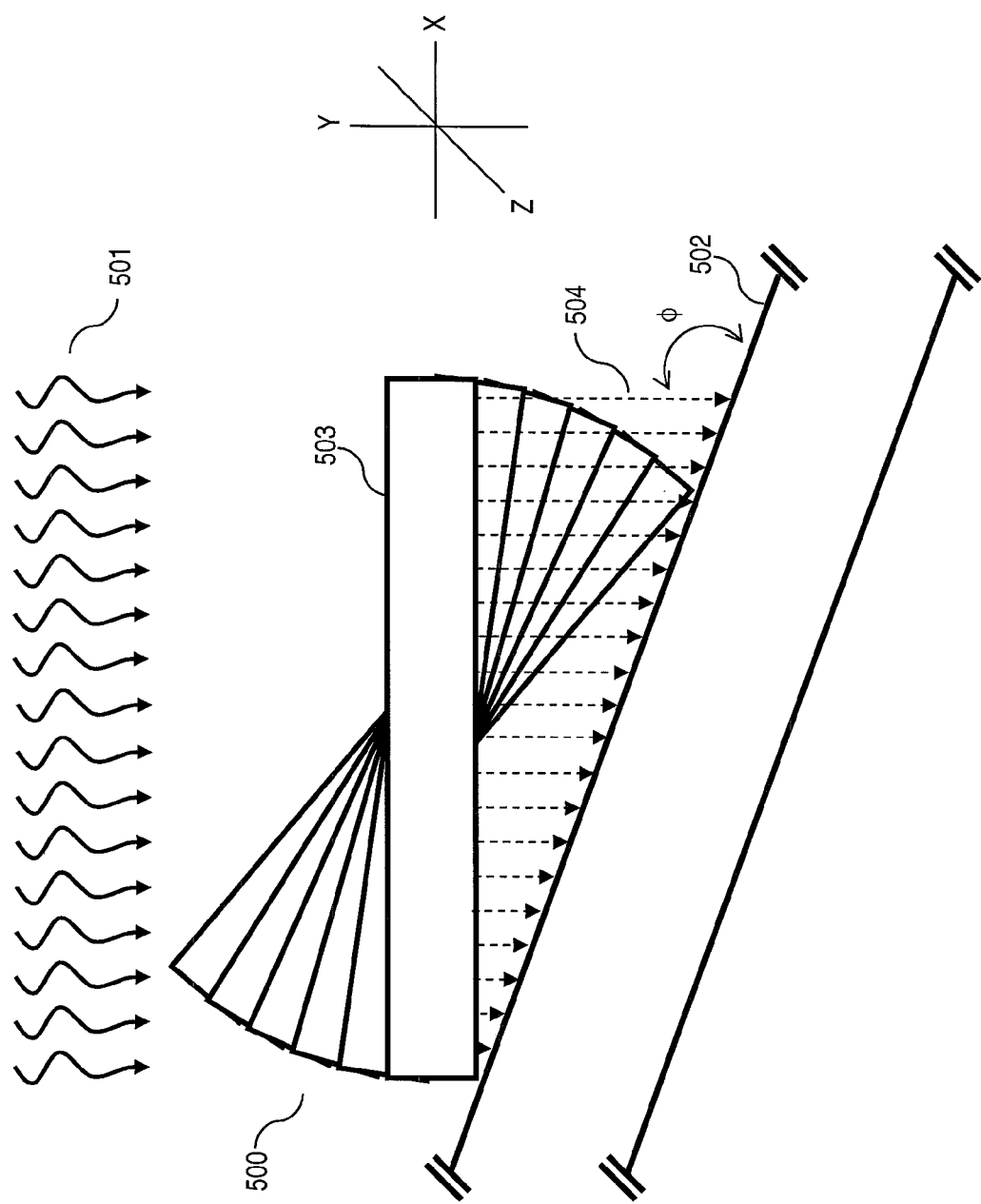
FIG. 5c is a side view schematically illustrating a twister type collimated radiation detector face of a detection ring, in accordance with an embodiment of the present invention.

FIG. 5c is a side view schematically illustrating a twister type collimated radiation detector face of a detection ring, in accordance with an embodiment of the present invention. As shown, a twister type collimator array 500 is positioned between a radiation ionizing subject (not shown) from which gamma quanta 501 is emanating and a detection face 502 of each of the plurality of radiation detection rings 102a-102d. The collimating surfaces of twister type collimator array 500 are spaced apart from the axial path of ionizing subject 103 at predefined distances, greater than the inner radius of stationary bore 104, and therefore, defining the maximum subject accommodation space available. Furthermore, each collimating bar of collimating array 500 collimates the emanating field of gamma quanta 501 such that corresponding bars create corresponding parallel beams of incidence upon face 502 at predefined angles of incidence. Exemplarily, horizontal bar 503 collimates gamma field 501 to create parallel beam 504 such that incident gamma quanta strike detection face 502 at an angle of incidence equivalent to $\phi$. In this manner, each collimating bar of collimating array 500 may create a different parallel beam with a different incident angle than that of an adjacent bar(s). Thus, the array of parallel beams created by the array of collimating bars corresponds to a plurality of angular views from which tomographic images may be reconstructed.

Thus, for system 100 employing four detection rings 102a-102b longitudinally and annularly displaced, comprising four individual detection faces at predetermined viewing radii, and collimated by twister type collimator arrays 500 of six collimating bars 500a-500f, 24 individual viewing angles are possible. Furthermore, incorporating collimator bars 500a-500f with aperture arrays including 4 to 7 rows of apertures, approximately 90 to 170 integral plane projection views are possible at each iterative step of table 105. Thus, a sufficient number of view points of the internal spatial distribution of the radiopharmaceutical within subject 103 are possible to generate adequate 3D radionuclide images of subject 103. As such, gantry 101 does not require (but may include) traditional radiation detectors that require an orbiting path about axis C-C to acquire sufficient imaging information. Therefore, embodiments of the present invention enable benefits such as: lowered gantry costs, increased reliability, and simplified calibration due to less mechanically operable components within the radionuclide imaging system.

The present invention enjoys industrial applicability in various types of nuclear medical imaging devices, including SPECT, CT, and PET. Advantageously, embodiments of the present invention enable the fabrication of any of the various types of nuclear medical imaging devices at a reduced cost by reducing the cost and complexity of conventional supporting and rotating detectors. Embodiments of the present invention include medical radionuclide imaging apparatuses that accommodate the use of lower cost, simplified gantries that do not require radiation detectors to orbit a subject to be imaged.

In the preceding description, the present invention is described with reference to specific exemplary embodiments thereof. It will, however, be evident that various modifications and changes may be made thereto without departing from the broader spirit and scope of the present invention, as set forth in the claims. The specification and drawings are, accordingly, to be regarded as illustrative and not as restrictive. It is understood that the present invention is capable of using various other combinations and embodiments and is capable of any changes or modifications within the scope of the inventive concept as expressed herein.

What is claimed is:

1. A collimator comprising a plurality of adjacently stacked collimating segments sharing a common central axis, each segment having a plurality of apertures extending therethrough, wherein adjacent collimating segments are annularly displaced from one another about the common central axis.

2. The collimator according to claim 1, wherein:
   each segment comprises two facial surfaces defining a depth dimension;
   the apertures extend through the depth dimension; and
   the segments are adjacently stacked with parallel facial surfaces.

3. The collimator according to claim 2, wherein each segment comprises:
   first and second side walls substantially normal to the facial surfaces;
   first and second end walls substantially normal to the facial surfaces; and
   a plurality of corrugated septa walls substantially normal to the facial surfaces, bounded by the first and second side walls, oriented parallel to the end walls, and positioned to define cross-sections of the plurality of apertures,
   wherein the apertures form a collimation angle between 0° and ±10° with respect to an imaginary normal line extending through the depth and central to the cross-section of individual apertures.

4. The collimator according to claim 3, wherein the collimation angle is between ±4° and ±6°.

5. The collimator according to claim 3, wherein:
   individual aperture cross-sections are hexagonal; and
   individual apertures are substantially parallel to one another in depth.

6. The collimator according to claim 3, wherein the plurality of septa walls define the plurality of apertures in adjacent rows and columns.

7. The collimator according to claim 1, wherein annular displacement from adjacent collimating segments about the common central axis is between 2° and 45°.

8. The collimator according to claim 1, wherein annular displacement from adjacent collimating segments about the common central axis is between 5° and 9°.

9. The collimator according to claim 1, wherein annular displacement from adjacent collimating segments is variable from segment to segment.

10. A detector comprising:
a first polygonal-shaped detection ring having the collimator according to claim 1 on at least two sides thereof.

11. A system for providing multi-angular single photon emission computed tomography (SPECT), the system comprising the detector according to claim 10.

12. The system according to claim 11, wherein:
each collimator is arranged to be positioned between a radiating mass within a patient and its associated detector and spaced apart from a translational path for the radiating mass; and
each aperture forms a passageway for radiation rays emanating from the radiating mass in a direction substantially aligned with a longitudinal axis of the respective passageway so that aligned radiation rays strike the detector.

13. The system according to claim 12, wherein:
each collimator is mounted on an instrument support assembly;
said instrument support assembly is associated with a motive means for effecting longitudinal relative motion between said instrument support assembly and a patient for taking multi-angular SPECT radiation sampling of the radiating mass in the patient utilizing the passageways, without relative rotation between the instrument support assembly and patient.

14. A radionuclide imaging method comprising:
positioning a patient having a radiating mass within a single photon emission computed tomography (SPECT) system and moving the patient along a longitudinal axis, the SPECT system comprising:
a polygonal shaped radiation detector; and
a collimator on at least two sides of the polygonal shaped detector, wherein the collimator comprises a plurality of adjacently stacked collimating segments sharing a common central axis, each segment having a plurality of apertures extending therethrough, wherein the adjacent collimating segments are angularly displaced from one another about the common central axis;
wherein each aperture forms a passageway for radiation rays emanating from the radiating mass in a direction substantially aligned with a longitudinal axis of the respected passageway so that aligned radiation rays strike the detector; and
motive means for effective longitudinal relative motion between the detector and the patient for taking multi-angular SPECT radiation sampling of the radiating mass in the patient utilizing the passageways, without relative rotation between the patient and detector.

15. The method according to claim 14, comprising:
administering a radiopharmaceutical to the patient;
linearly displacing the patient through a series of the radiation detectors including one or more stationary gamma cameras configured to detect gamma rays emanating from the patient;
collimating gamma rays emanating from the patient through a series of the stacked collimating segments positioned between the patient and the one or more gamma cameras; and
recording gamma ray occurrences detected at the one or more gamma cameras.

16. A nuclear medical imaging apparatus comprising:
a gantry defining a central longitudinal axis;
a plurality of detection rings disposed about the axis and supported by the gantry;
and a plurality of radiation detectors disposed among the plurality of detection rings and configured to detect ionizing radiation,
wherein the adjacent rings are longitudinally and annularly displaced from one another along the axis, and
wherein at least one collimator is disposed between the subject ionizing radiation and one or more of the plurality of radiation detectors, the at least one collimator comprising a plurality of adjacently stacked collimating segments sharing a common central axis, each segment having a plurality of apertures extending therethrough, wherein adjacent collimating segments are annularly displaced from one another about the common central axis.

17. The apparatus according to claim 16, the gantry further comprising:
an optically opaque bore of a predefined diameter and transmissive to ionizing radiation originating within an enclosed bore volume, the bore configured to receive a subject ionizing radiation.

18. The apparatus according to claim 17, wherein each detection ring comprises:
a first and second outer surface defining a longitudinal depth, the outer surfaces being parallel to an axial plane perpendicular to the axis; and
at least one inner surface at a radial displacement from the axis and configured to support one or more of the radiation detectors.

19. The apparatus according to claim 18, wherein the outer surfaces of individual detection rings substantially abut one another to form a relatively contiguous detection entity.

* * * * *